(12) United States Patent
van der Merwe et al.

(10) Patent No.: US 10,130,304 B2
(45) Date of Patent: *Nov. 20, 2018

(54) SYSTEM, METHOD AND APPARATUS FOR ORIENTATION CONTROL

(71) Applicant: DEKA Products Limited Partnership, Manchester, NH (US)

(72) Inventors: Dirk Albertus van der Merwe, Canterbury, NH (US); Thomas A. Doyon, Manchester, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/840,559

(22) Filed: Aug. 31, 2015

(65) Prior Publication Data

US 2015/0366505 A1 Dec. 24, 2015

Related U.S. Application Data

(63) Continuation of application No. 13/907,030, filed on May 31, 2013, now Pat. No. 9,121,699, which is a
(Continued)

(51) Int. Cl.
*A61B 5/103* (2006.01)
*A61B 5/00* (2006.01)
(Continued)

(52) U.S. Cl.
CPC .............. *A61B 5/6807* (2013.01); *A61B 5/11* (2013.01); *A61F 2/68* (2013.01); *A61F 2/72* (2013.01);
(Continued)

(58) Field of Classification Search
CPC ..................................... G01C 9/00; A61F 2/58
(Continued)

(56) References Cited

U.S. PATENT DOCUMENTS 4,841,773 A 6/1989 Stewart
5,252,102 A 10/1993 Singer et al.
(Continued)

FOREIGN PATENT DOCUMENTS

WO 02/00158 A2 1/2002
WO 2009/155595 A2 12/2009

OTHER PUBLICATIONS

Invitation to Pay Additional Fees and, Where Applicable, Protest Fee including Partial Search Report from corresponding International Appln. No. PCT/US2016/043864 dated Nov. 11, 2016 (7 pages).
(Continued)

*Primary Examiner* — G. Bradley Bennett
(74) *Attorney, Agent, or Firm* — McCormick, Paulding & Huber LLP

(57) ABSTRACT

A system for control of a device includes at least one sensor module detecting orientation of a user's body part. The at least one sensor module is in communication with a device module configured to command an associated device. The at least one sensor module detects orientation of the body part. The at least one sensor module sends output signals related to orientation of the user's body part to the device module and the device module controls the associated device based on the signals from the at least one sensor module.

20 Claims, 8 Drawing Sheets

Related U.S. Application Data continuation of application No. 12/706,471, filed on Feb. 16, 2010, now Pat. No. 8,453,340, which is a continuation-in-part of application No. 12/027,116, filed on Feb. 6, 2008, now Pat. No. 8,821,587.

(60) Provisional application No. 60/899,834, filed on Feb. 6, 2007, provisional application No. 60/963,638, filed on Aug. 6, 2007, provisional application No. 61/168,832, filed on Apr. 13, 2009, provisional application No. 61/221,858, filed on Jun. 30, 2009.

(51) Int. Cl.

| | |
|---|---|
| *A61F 2/72* | (2006.01) |
| *A61F 2/76* | (2006.01) |
| *G01C 21/16* | (2006.01) |
| *A61B 5/11* | (2006.01) |
| *G01C 9/00* | (2006.01) |
| *G05B 15/02* | (2006.01) |
| *A61F 2/68* | (2006.01) |
| *A61F 2/70* | (2006.01) |
| *A61B 5/0488* | (2006.01) |
| *A61F 2/54* | (2006.01) |
| *A61F 2/60* | (2006.01) |

(52) U.S. Cl.
CPC ............... *A61F 2/76* (2013.01); *G01C 9/00* (2013.01); *G01C 21/16* (2013.01); *G05B 15/02* (2013.01); *A61B 5/0488* (2013.01); *A61B 5/1036* (2013.01); *A61B 5/4528* (2013.01); *A61F 2/54* (2013.01); *A61F 2/60* (2013.01); *A61F 2002/6827* (2013.01); *A61F 2002/701* (2013.01); *A61F 2002/704* (2013.01); *A61F 2002/705* (2013.01); *A61F 2002/707* (2013.01); *A61F 2002/762* (2013.01); *A61F 2002/763* (2013.01); *A61F 2002/764* (2013.01); *A61F 2002/765* (2013.01); *A61F 2002/7625* (2013.01); *A61F 2002/7635* (2013.01); *A61F 2002/7685* (2013.01)

(58) Field of Classification Search
USPC .................................. 33/316, 318, 324, 512
See application file for complete search history.

(56) References Cited

U.S. PATENT DOCUMENTS

| | | | |
|---|---|---|---|
| 5,617,595 A | 4/1997 | Landi et al. | |
| 5,748,845 A | 5/1998 | Labun et al. | |
| 5,881,609 A | 3/1999 | Palmer | |
| 6,685,661 B2 | 2/2004 | Peled | |
| 7,186,270 B2* | 3/2007 | Elkins | A61F 2/68 200/86.5 |
| 8,430,578 B1* | 4/2013 | Theriault | G01C 19/5783 33/275 G |
| 8,453,340 B2* | 6/2013 | van der Merwe | A61B 5/1038 33/512 |
| 8,821,587 B2* | 9/2014 | Lanier | A61F 2/68 600/587 |
| 9,114,028 B2 | 8/2015 | Langenfeld et al. | |
| 9,121,699 B2* | 9/2015 | van der Merwe | A61B 5/1038 |
| 2003/0018388 A1 | 1/2003 | Comer | |
| 2004/0064286 A1* | 4/2004 | Levi | G01C 21/12 702/141 |
| 2004/0267379 A1 | 12/2004 | Pasolini | |
| 2005/0177952 A1 | 8/2005 | Wilkinson et al. | |
| 2005/0256507 A1 | 11/2005 | Long et al. | |
| 2006/0135883 A1 | 6/2006 | Jonsson et al. | |
| 2008/0078033 A1 | 4/2008 | Wyatt et al. | |
| 2008/0288088 A1* | 11/2008 | Langenfeld | A61F 2/54 623/57 |
| 2011/0257765 A1* | 10/2011 | Evans | A61F 2/54 623/24 |
| 2012/0123558 A1* | 5/2012 | Gill | A61F 2/586 623/24 |

OTHER PUBLICATIONS

Lee et al., "A Composite Discrete/Continuous Control of Robot Manipulators", Apr. 1991, Carnegie Mellon University: The Robotics Institute, Pittsburg, PA, pp. 1-21.

* cited by examiner

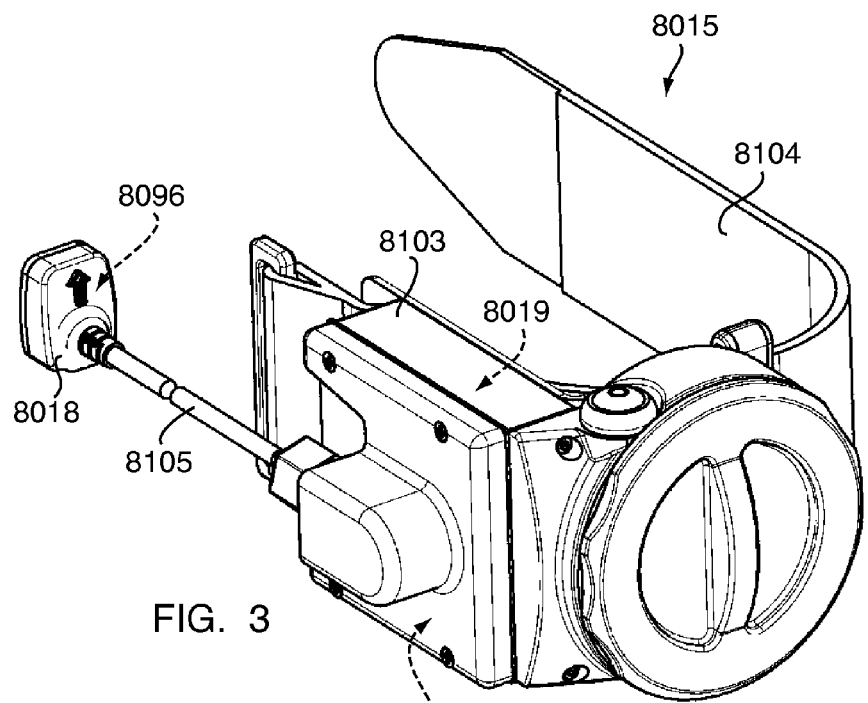
FIG. 3
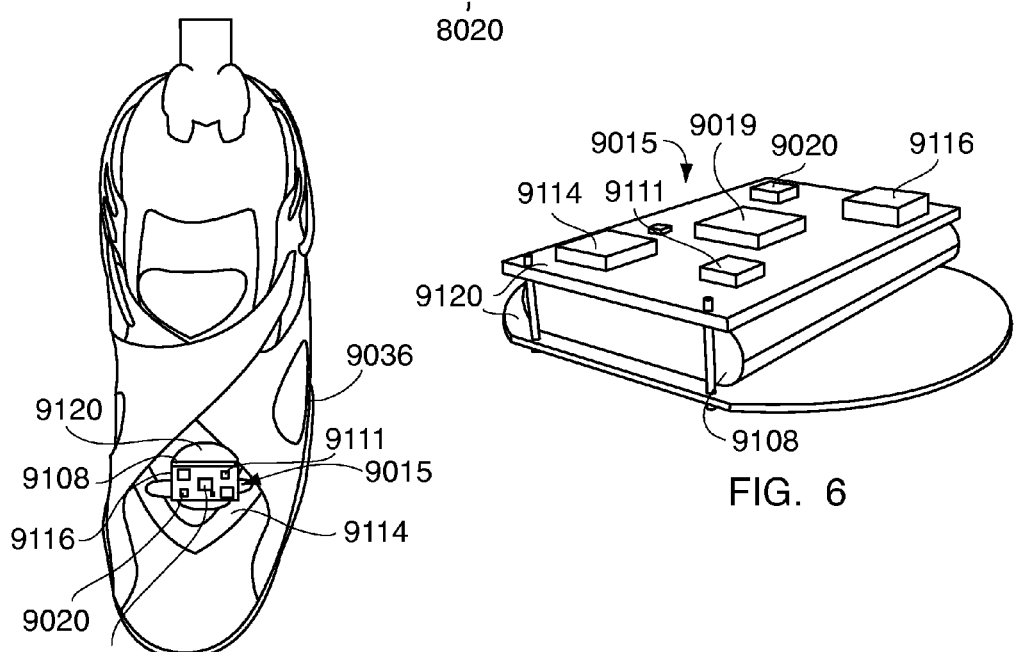
FIG. 5
FIG. 6 though the use of such terms and expressions, of excluding any equivalents of the features shown and described or portions thereof, it being recognized that various modifications are possible within the scope of the invention claimed.

SYSTEM, METHOD AND APPARATUS FOR ORIENTATION CONTROL

CROSS-REFERENCE TO RELATED APPLICATIONS

This application is a continuation of U.S. patent application Ser. No. 13/907,030, filed May 31, 2013, which is a continuation of U.S. patent application Ser. No. 12/706,471, filed Feb. 16, 2010, which is a continuation-in-part of U.S. patent application Ser. No. 12/027,116, filed Feb. 6, 2008, which claims priority from U.S. Provisional Patent Application Ser. No. 60/899,834, filed Feb. 6, 2007, and U.S. Provisional Patent Application Ser. No. 60/963,638, filed Aug. 6, 2007, each of which is hereby incorporated by reference in its entirety. This application also claims priority to U.S. Provisional Patent Application Ser. No. 61/168,832, filed Apr. 13, 2009, and U.S. Provisional Patent Application Ser. No. 61/221,858, filed Jun. 30, 2009, each of which is also hereby incorporated by reference in its entirety.

TECHNICAL FIELD

The present invention relates to a system, method and apparatus for control of a device and more particularly, to a system, method and apparatus for orientation control of the device.

BACKGROUND INFORMATION

Many remote controls have been designed to manipulate robotic devices, mechanical devices, and virtual devices. There is a desire for a control system that may process user signals quickly and accurately while providing smooth directional and proportional control of associated objects.

SUMMARY

In accordance with one aspect of the present invention, a control apparatus for a device is disclosed. The control apparatus includes at least one sensor module having an inertial measurement unit and at least one device module in communication with the at least one sensor module. The at least one sensor module is adapted to be worn by a user on at least one body part with the inertial measurement unit detecting body input and transmitting the body input to the device module. The device module translates the body input into an orientation of the at least one body part and commands the device based on the orientation.

In accordance with another aspect of the invention, the at least one sensor module is disposed in footwear.

In accordance with another aspect of the invention, the at least one sensor module is in wireless communication with the device module. In accordance with a further aspect of the invention, the device module is in wireless communication with the device.

In accordance with another aspect of the present invention, a method for controlling the device is disclosed. The method comprises sensing body input and communicating the sensed body input to a device module. The method also includes translating the body input into a body orientation and controlling the device based on the orientation.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 3 is a side perspective view of another embodiment of a sensor module according to the present invention;

FIG. 5 is a top perspective view of a sensor module according to another embodiment of the present invention;

FIG. 6 is an enlarged side perspective view of the sensor module of FIG. 5;

DETAILED DESCRIPTION OF THE PREFERRED EMBODIMENTS

Figure 1A:
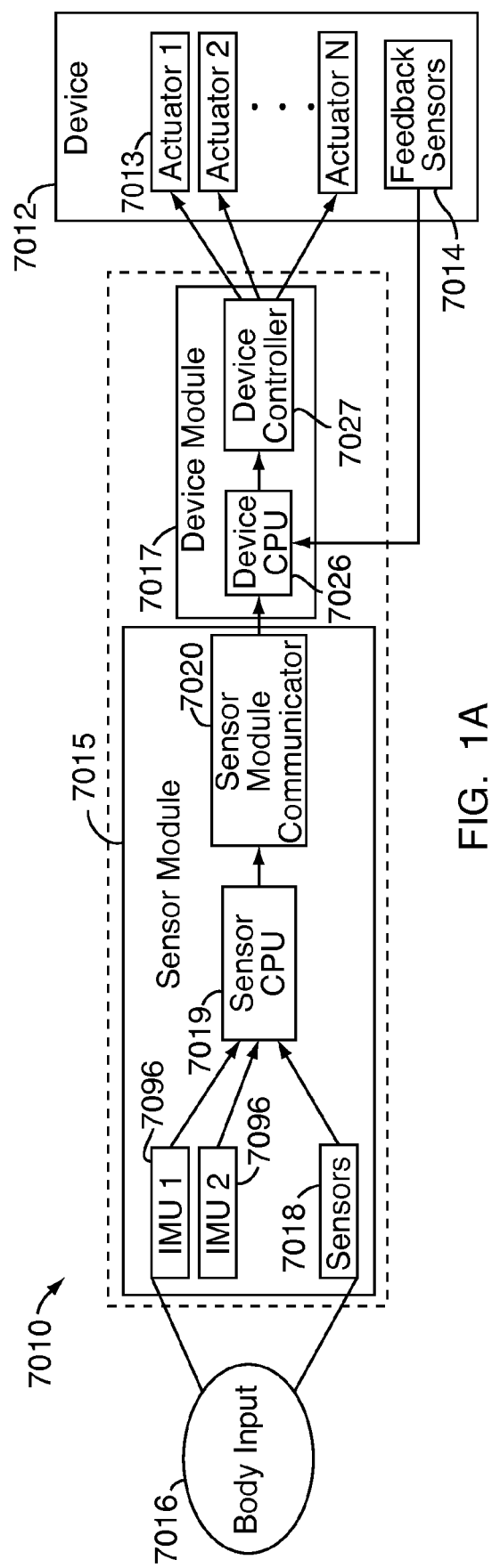
FIG. 1A is a schematic diagram of a prosthetic control apparatus according to another embodiment of the present invention.

Referring to FIG. 1A, a schematic view of a control system 7010 for an associated device 7012 is shown. The control apparatus 7010 comprises a sensor module 7015 for detecting body input 7016 and a device module 7017 for commanding the associated device 7012. The associated device 7012 may be, for example, an arm prosthetic device such as those disclosed in U.S. patent application Ser. No. 12/027,141, filed Feb. 6, 2008, and the U.S. patent application Ser. No. 12/706,609, filed Feb. 16, 2010, each of which is hereby incorporated by reference in its entirety. Additionally, the present invention is suitable for use in a variety control systems, such as those disclosed in U.S. application Ser. No. 12/706,575, filed Feb. 16, 2010, which is also hereby incorporated by reference in its entirety.

The sensor module 7015 includes one or more Inertial Measurement Units (IMUs) 7096 connected to a sensor central processing unit (sensor CPU) 7019 that is connected to a sensor module communicator 7020. The one or more IMUs 7096 detect orientation, as will be discussed in greater detail below, which may be transmitted to device module 7017 for controlling the associated device 7012. The sensor CPU 7019 inputs data from the one or more IMUs 7096 and filters and/or converts the data to generate orientation signals. The orientation signals are then sent to the device module 7017 by the sensor module communicator 7020. The sensor module communicator 7020 may be hard wired to the device module 7017 or may transmit the user input signals wirelessly, for example, but not limited to, through a radio transmitter, Bluetooth® or the like. Thus, by altering the orientation of the one or more IMUs 7096, the user may control the device 7012 in a desired manner. The sensor module may also include one or more sensors 7018 adapted to be disposed at various locations on the user to sense additional body input 7016 from the user.

In some embodiments, the device module 7017 includes a device CPU 7026 connected to a device controller 7027. The device CPU 7026 receives the orientation signals from the sensor module communicator 7020. Based on the orientation signals from the sensor module communicator 7020, the device CPU 7026 calculates device commands that are sent to the associated device 7012 by the device controller 7027 to control the device.

Figure 1B:
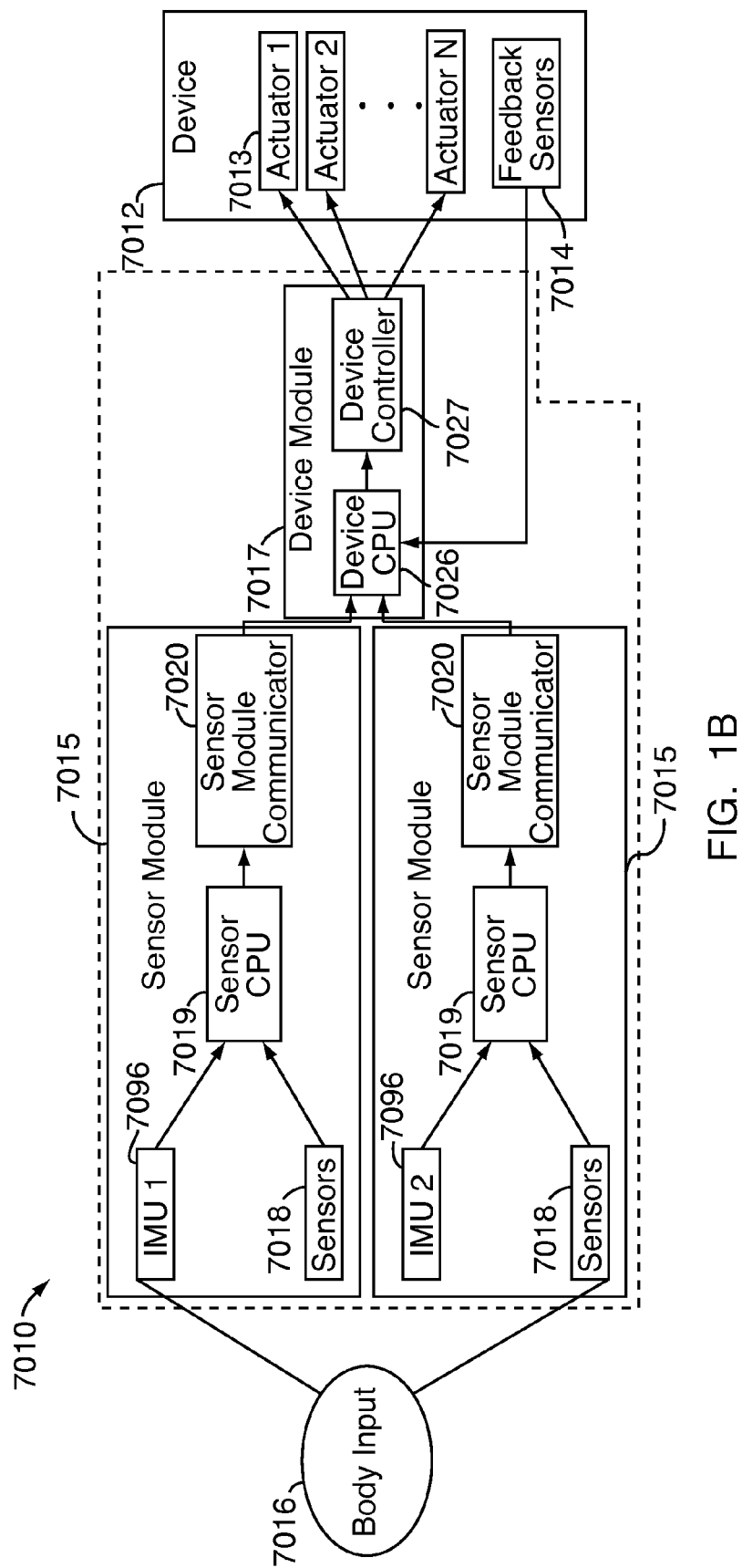
FIG. 1B is another embodiment of the prosthetic control apparatus of FIG. 1A.

Referring to FIG. 1B, in some embodiments where multiple IMUs 7096 are attached to different body parts, it may be desirable to provide separate sensor modules 7015 for each IMU 7096 to decouple to IMUs 7096 from each other. In these embodiments, each sensor module 7015 may communicate with the device module 7017 and the device module 7017 uses the orientation signals provided from each sensor module 7015 to command the associated device 7012.

Figure 2:
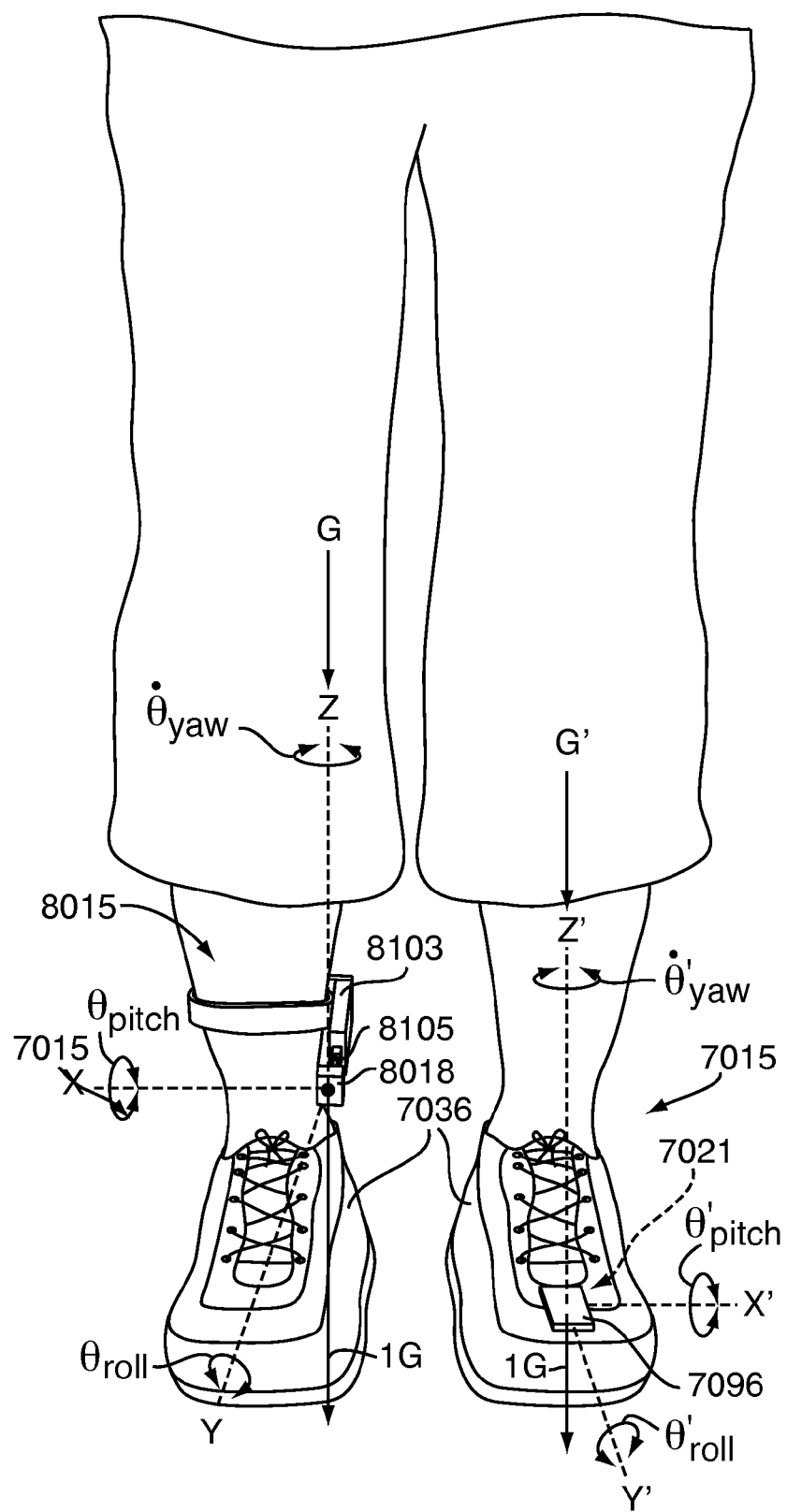
FIG. 2 is a front perspective view of two sensor modules of FIG. 1B being used by a user.
Figure 4:
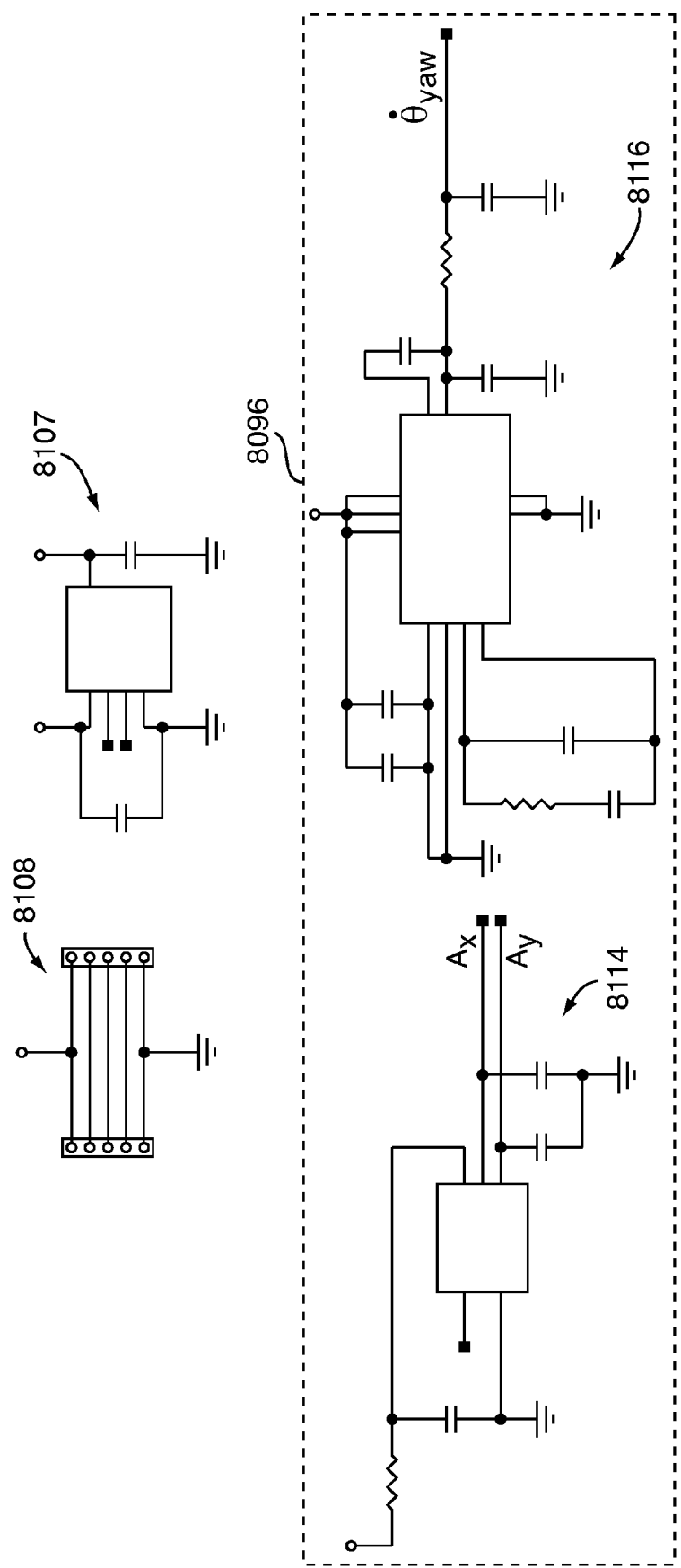
FIG. 4 is an electrical schematic of one embodiment of an inertial measurement unit.

Referring to FIG. 2, in some embodiments, the IMU 7096 may determine the orientation of the user's foot 7021. In some embodiments, particularly where an increased number of control inputs is desired, one IMU 7096 may be used on each foot 7021 of the user (the term "feet" or "foot" is a general description, in some embodiments, the IMU 7096 may be placed on a user's ankle or ankles or on the user's leg or legs. In some embodiments, the IMU(s) 7096 may be placed on any part of a user indicative of the movement of the foot/feet, including, but not limited to, affixed to the user's clothing or footwear 7036). In some embodiments, IMUs 7096 may be placed at other locations on the user including but not limited to the user's arm, head, or the like. Each IMU 7096 is a device capable of sensing motion using a combination of sensors as will be discussed in greater detail below. Referring to FIG. 4, wherein like numerals represent like elements, the IMU 8096 may include one or more accelerometers 8114 and/or one or more gyroscopes 8116, to measure orientation of the IMU 8096 relative to a gravitational direction G, shown in FIG. 2, including, but not limited to, sensing type, rate, and direction of the orientation change of the IMU 8096.

Referring to FIG. 3, in some embodiments, the sensor module 8015 may include a main housing portion 8103 having a strap 8104 to allow the sensor module 8015 to be attached to the user's foot, ankle or other body part. The main housing portion 8103 has a wiring conduit 8105 extending outwardly therefrom to an IMU housing 8098. The main housing portion 8103 accommodates the sensor CPU 8019 and the sensor module communicator 8020. Referring to FIG. 4, the main housing portion 8103 may also accommodate a power supply 8107 for powering the sensor module 8015. The IMU housing 8098, shown in FIG. 3, accommodates the IMU 8096, which may include the two-axis accelerometer 8114 and the yaw rate gyroscope 8116. As used herein, the term two-axis accelerometer 8114 should be understood to include devices capable of detecting accelerations in two axes, i.e. the X and Y axes shown in FIG. 2, and is synonymous with two single axis accelerometers, which are each capable of detecting accelerations about a single axis, i.e. the X axis or the Y axis, shown in FIG. 2. The IMU 8096 in the IMU housing 8098 is operatively connected to the sensor CPU 8019, the sensor module communicator 7020 and the power supply 8107 by connectors 8108, which extend through the wiring conduit 8105, shown in FIG. 3. Referring back to FIG. 3, connecting the IMU housing 8098 to the main housing portion 8103 through the conduit 8105 is advantageous because it allows the IMU 8096 to be positioned away from the user's foot or ankle. Thus, a small orientation change at the user's foot or ankle will cause a greater orientation change at the IMU housing 8098, which may be more readily detected by the IMU 8096.

In the embodiment of the IMU(s) 8096 shown in FIG. 4, the IMU 8096 captures data relating to only orientation, rather than in some other embodiments, where the IMU(s) captures data relating to both orientation and position. Specifically, in this embodiment, the sensor module 8015 produces and transmits to the device module 7017, shown in FIGS. 1A and 1B, three (3) raw signals relating to pitch, roll and yaw and the device module 7017 uses these signals to command the associated device 7012, shown in FIGS. 1A and 1B, as will be discussed in greater detail below. Although shown as including the two-axis accelerometer 8114 and the yaw rate gyroscope 8116, in various other embodiments, the IMU 8096 may include three (3) gyroscopes 8116 and no accelerometers 8114. Using three (3) gyroscopes, the algorithm used by the device module 7017, shown in FIGS. 1A and 1B, to control the associated device based on yaw, discussed in greater detail below, would be used for the other two (2) axes to command movement based on pitch rate and roll rate.

The gyroscopes 8116 may provide many benefits over the use of accelerometers 8114. These include but are not limited to some of the following. A single algorithm may be used to estimate the Euler angles for all three axes, X, Y and Z. The gyroscopes 8116 are less sensitive to use in a non-inertial frame (e.g., car, boat, etc.) compared with accelerometers 8114. Additionally, there are no dynamic range/resolution issues due to initial inclination when control angle is re-zeroed, which may be present with accelerometers 8114. Additionally, in embodiments using three (3) accelerometers 8114 and/or gyroscopes 8116, user walking may be detected using a threshold rate with the assumption that the user moves their foot faster when walking than when controlling the associated device 7012, shown in FIGS. 1A and 1B.

However, in some embodiments, the IMU 8096 having two accelerometers 8114 (or a two-axis accelerometer) and one gyroscope 8116 may be preferable over embodiments having three gyroscopes 8116 for reasons that may include, but are not limited to, any one or more of the following. The orientation signal provided by gyroscopes 8116 may drift over time, while there is no need to de-drift accelerometer axes. It may be simpler for the sensor CPU 8019 to estimate Euler angles using accelerometers 8114 than it is using gyroscopes 8116. In particular, the algorithm used by the sensor CPU 8019 for processing signals from the accelerometers 8114 requires less processing power than gyroscopes 8116. This may be particularly advantageous in many situations including with respect to use of the IMU(s) 8096 to control a prosthetic arm where the sensor module(s) 8019 are located on the user's ankle(s), where it may be advantageous and desirable to employ a wireless signal transfer between the sensor module 8019 and the device module 7017, shown in FIGS. 1A and 1B. Thus, in these and other embodiments, it may be desirable to use a smaller sensor CPU 8019 based on power usage and size and using two accelerometers 8114 and one gyroscope 8116, rather than three gyroscopes 8116, may allow the use of the smaller sensor CPU 8019.

Additionally, the accelerometers 8114 may themselves draw less power and be smaller in size than gyroscopes 8116. Also, the accelerometers 8114 may not require a specific DC range for power, which may allow for use of a non-changing and smaller range.

As discussed above, in some embodiments, the sensor CPU 8019 may filter the signals collected by the IMU 8096 to remove sensor noise and to provide a more clean signal. However, providing this functionality may result in a sensor module 8015 that is large and/or heavy and/or has large power requirements. Thus, it may be desirable, in some embodiments, to use a sensor module 8015 with less functionality that includes the capability of collecting "raw" data that may be used to determine pitch, roll and yaw. For instance, in some embodiments, the sensor module 7015, shown in FIGS. 1A and 1B, may include only three accelerometers 8114 and no gyroscope 8116. Since this sensor module 7015, shown in FIGS. 1A and 1B, will have less functionality, the measurements collected by the sensor module 7015, shown in FIGS. 1A and 1B, may be translated to 3-dimensional measurements by device module 7017, shown in FIGS. 1A and 1B.

In some embodiments, the power supply 8107, shown in FIG. 4, may be a regenerative energy device, for instance, the power supply 8107 may be recharged by kinetic movement, e.g., walking. In the exemplary embodiment, the power requirement for the sensor module 8015 is approximately seven (7) milliamps.

Referring to FIGS. 5 and 6, in some embodiments, the sensor module 9015 may be a single unit adapted to be attached to the user's footwear 9036, shown in FIG. 5. The sensor module 9015 may include gyroscope 9116, three-axis accelerometer 9114, sensor CPU 9019, sensor module communicator 9020 and sensor power supply 9107 all attached to a support structure formed of one or more circuit boards 9120. The sensor power supply 9107 may include a battery 9108 and a wireless power antenna 9111, connected to the battery 9018, for wirelessly charging the battery 9108 by associating it with a wireless charger, such as a charging pad, or by any other wireless charging system known in the art. Alternatively, the battery may be charged directly through a charger plug (not shown). In some embodiments, the battery 9108 may be charged during use through the wireless power antenna 9111. The sensor power supply 9107 is substantially smaller than the power supplies discussed in previous embodiments, providing for a smaller sensor module 9015. Additionally, since the sensor module 9015 includes the three-axis accelerometer 9114, the sensor module 9015 is capable of detecting accelerations about three axes, which may advantageously facilitate walk detection, as will be discussed in greater detail below. It should be understood that the term three-axis accelerometer, as used herein, is a single orientation sensor capable of measuring three perpendicular axes or acceleration and is interchangeable with three separate accelerometers arranged on three perpendicular axes.

Referring back to FIG. 2, the data collected from the at least one IMU 7096 may be used by the device module 7017, shown in FIGS. 1A and 1B, in an algorithm to translate orientation of the foot 7021 and/or changes in orientation to a commanded control of the associated device 7012, shown in FIGS. 1A and 1B. In some embodiments, IMU 7096 may include at least two accelerometers 8114, shown in FIG. 4 detecting acceleration about two axes and at least one gyroscope 8116, shown in FIG. 4, for detecting orientation changes about a third axis. Thus, the IMU 7096, in some embodiments, may detect orientation changes about at least three axes, thereby allowing the user to control the associated device 7012, shown in FIGS. 1A and 1B, in at least three degrees of freedom.

The accelerometers 8114, shown in FIG. 4, of each of the IMUs 7096 may be arranged to detect pitch $\theta_{Pitch}$ about the X axis relative to the gravitational direction G and roll $\theta_{Roll}$ about the Y axis relative to the gravitational direction G. The gyroscope 8116, shown in FIG. 4, of each of the IMUs 7096 is, in some embodiments, arranged to detect yaw $\dot{\theta}_{Yaw}$ about the Z axis. Thus, by using two IMUs 7096, one IMU 7096 on each foot 7021, the user is able to control the associated device 7012, shown in FIGS. 1A and 1B, in at least six degrees of freedom.

Each IMU 7096 is arranged with one accelerometer 8114, shown in FIG. 4, in the Y direction and the other accelerometer 8114, shown in FIG. 4, in the X direction. When the IMU 7096 is flat, i.e. the Z axis is coincident with the gravitational direction G, gravity, which is an acceleration of 1G in the gravitational direction G, only includes a component projected on the Z axis. As the IMU 7096 tilts, a component of gravity is projected onto the X axis and/or Y axis. This tilt is detectable by the accelerometer 8114, shown in FIG. 4, arranged on the axis upon which the component of gravity is projected. Since 1G is a known value, the arcsin of the value detected by each accelerometer 8114, shown in FIG. 4, of the IMU 7096 is a proportion of 1G and representative of the pitch $\theta_{Pitch}$ and/or roll $\theta_{Roll}$.

Figure 7:
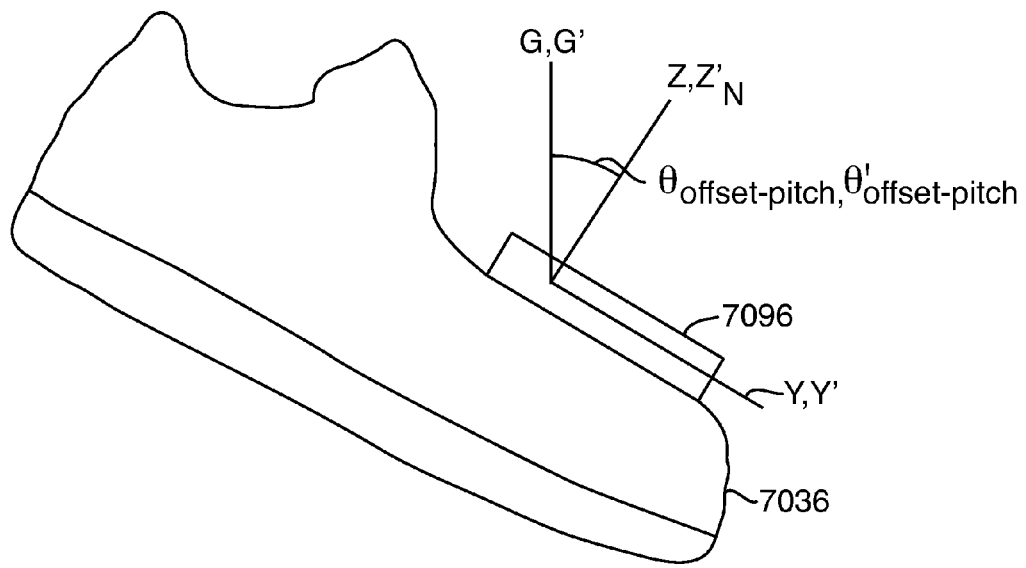
FIG. 7 is a side view of an inertial measurement unit of FIG. 2 tilted forward.
Figure 8:
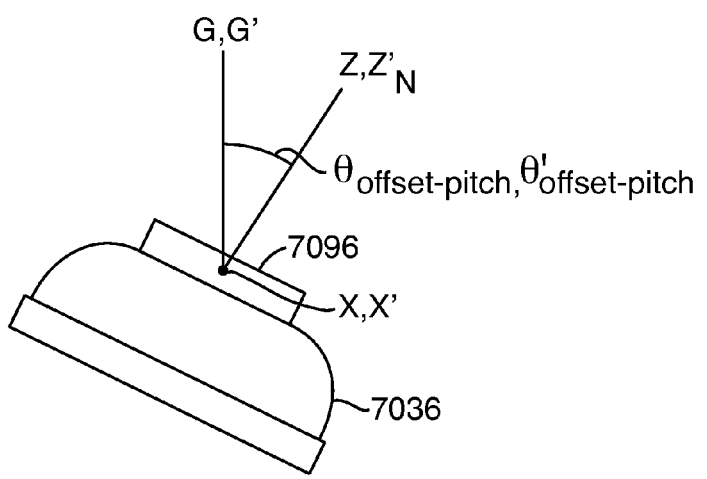
FIG. 8 is a front view of an inertial measurement unit of FIG. 2 tilted sideways.

Although shown in FIG. 2 with the Z axis being coincident with the gravitational direction G, as seen in FIGS. 7 and 8, the Z axis of each of the IMUs 7096 may be offset from the gravitational direction G; for example, if the IMU 7096 is not initially situated flatly on the users foot 7021, if the IMU 7096 shifts during use, or if the user is standing on an incline, decline or the like. Therefore, the sensor module 7015 of the present invention may zero the IMUs 7096 by setting a pitch offset, $\theta_{Offset\_Pitch}$, and a roll offset, $\theta_{Offset\_Roll}$, when initialized or reinitialized during use.

Figure 9:
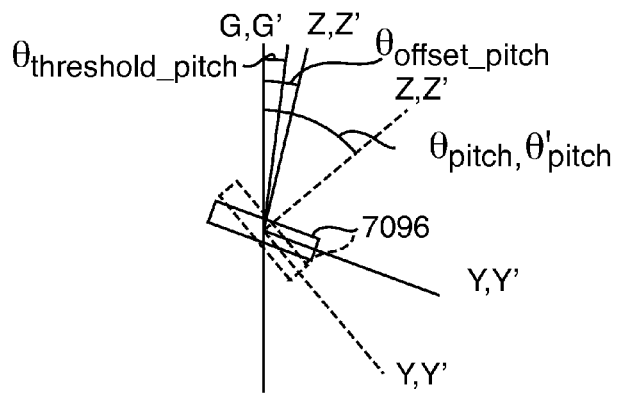
FIG. 9 is side view of the inertial measurement unit of FIG. 7.

Referring to FIG. 9, the pitch $\theta_{Pitch}$ detected by the IMU 7096 may be configured to command the associated device 7012, shown in FIGS. 1A and 1B. For example, the device module 7017, shown in FIGS. 1A and 1B, may command the associated device when:

$$|\theta_{Pitch} - \theta_{Offset\_Pitch}| \geq \theta_{Threshold\_Pitch}$$

where, $\theta_{Pitch}$ is the pitch detected by the IMU 7096 relative to the gravitational direction G;

$\theta_{Offset\_Pitch}$ is the preset value calibrating the IMU 7096 discussed above; and $\theta_{Threshold\_Pitch}$ is a present minimum pitch angle that must be exceeded to ensure that the detected pitch $\theta_{Pitch\_}$ is a desired command and not due to unintentional movement of the user's foot 7021, shown in FIG. 2.

In one embodiment, the command generated by the device module 7017, shown in FIGS. 1A and 1B, from the pitch $\theta_{Pitch}$ may be a switch that alternates between an "on state" and an "off state" each time $|\theta_{Pitch} - \theta_{Offset\_Pitch}| \geq \theta_{Threshold\_Pitch}$. In another embodiment, pitch $\theta_{Pitch}$ may command the device module 7017 to toggle through a list. For example, each instance that $\theta_{Threshold\_Pitch}$ is exceeded, the device module 7017 may toggle forward through the list if $(\theta_{Pitch} - \theta_{Offset\_Pitch})$ is a positive value and may toggle backward, i.e. in reverse, through the list if $(\theta_{Pitch} - \theta_{Offset\_Pitch})$ is a negative value.

In one embodiment, the command generated by the device module 7017, shown in FIGS. 1A and 1B, may correspond to a movement, $M_{Pitch}$, of the associated device 7012, shown in FIGS. 1A and 1B, if $|\theta_{Pitch}-\theta_{Offset\_Pitch}| \geq \theta_{Threshold\_Pitch}$. For example, when $|\theta_{Pitch}-\theta_{Offset\_Pitch}| \geq \theta_{Threshold\_Pitch}$ the device module 7017, shown in FIGS. 1A and 1B, may command movement at a preset velocity in a preset direction, e.g. the device module 7017 may command upward movement at the preset velocity if $(\theta_{Pitch}-\theta_{Offset\_Pitch})$ is a positive value and may command downward movement if $(\theta_{Pitch}-\theta_{Offset\_Pitch})$ is a negative value. In another embodiment, the movement may be commanded using the equation:

$$M_{Pitch}=k_1(\theta_{Pitch}-\theta_{Offset\_Pitch})+k_2$$

where, $k_1$ and $k_2$ are gains that may be preset based on the type of movement desired. The movement $M_{Pitch}$ may be set to correspond to a variety of possible movements of the associated device 7012, shown in FIGS. 1A and 1B. For example, $M_{Pitch}$ may be a distance of deflection in a direct direction or a speed of travel in a direction.

Figure 10:
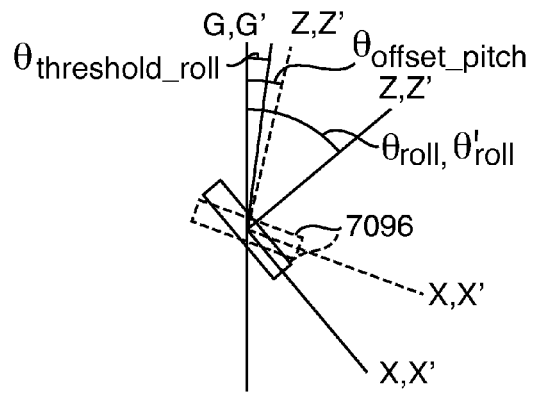
FIG. 10 is a front view of the inertial measurement unit of FIG. 8.

Referring to FIG. 10, the roll $\theta_{Roll}$ detected by the IMU 7096 may also be configured to command the associated device 7012, shown in FIGS. 1A and 1B, in a manner similar to that discussed above for the pitch $\theta_{Pitch}$. For example, the device module 7017, shown in FIGS. 1A and 1B, may command the associated device when:

$$|\theta_{Roll}-\theta_{Offset\_Roll}| \geq \theta_{Threshold\_Roll}$$

where, $\theta_{Roll}$ is the roll detected by the IMU 7096 relative to the gravitational direction G;

$\theta_{Offset\_Roll}$ is the preset value calibrating the IMU 7096 discussed above; and $\theta_{Threshold\_Roll}$ is a present minimum roll angle that must be exceeded to ensure that the detected roll $\theta_{Roll}$ is a desired command and not due to unintentional movement of the user's foot 7021, shown in FIG. 2.

In one embodiment, the command generated by the device module 7017, shown in FIGS. 1A and 1B, from the roll $\theta_{Roll}$ may be a switch that alternates between an "on state" and an "off state" each time $|\theta_{Roll}-\theta_{Offset\_Roll}| \geq \theta_{Threshold\_Roll}$. In another embodiment, roll $\theta_{Roll}$ may command the device module 7017, shown in FIGS. 1A and 1B, to toggle through a list. For example, each instance that $\theta_{Threshold\_Roll}$ is exceeded, the device module 7017, shown in FIGS. 1A and 1B, may toggle forward through the list if $(\theta_{Roll}-\theta_{Offset\_Roll})$ is a positive value and may toggle backward, i.e. in reverse, through the list if $(\theta_{Roll}-\theta_{Offset\_Roll})$ is a negative value.

In one embodiment, the command generated by the device module 7017, shown in FIGS. 1A and 1B, may correspond to a movement, $M_{Roll}$, of the associated device 7012, shown in FIGS. 1A and 1B, if $|\theta_{Roll}-\theta_{Offset\_Roll}| \geq \theta_{Threshold\_Roll}$. For example, when $|\theta_{Roll}-\theta_{Offset\_Roll}| \geq \theta_{Threshold\_Roll}$ the device module 7017, shown in FIGS. 1A and 1B, may command movement at a preset velocity in a preset direction, e.g. the device module 7017 may command movement to the right at the preset velocity if $(\theta_{Roll}-\theta_{Offset\_roll})$ is a positive value and may command movement to the left if $(\theta_{Roll}-\theta_{Offset\_Roll})$ is a negative value. In another embodiment, the movement may be commanded using the equation:

$$M_{Roll}=k_3(\theta_{Roll}-\theta_{Offset\_Roll})+k_4$$

where, $k_3$ and $k_4$ are gains that may be preset based on the type of movement desired. The movement $M_{Roll}$ may be set to correspond to a variety of possible movements of the associated device 7012, shown in FIGS. 1A and 1B. For example, $M_{Roll}$ may be a distance of deflection in a direct direction or a speed of travel in a direction.

Figure 11:
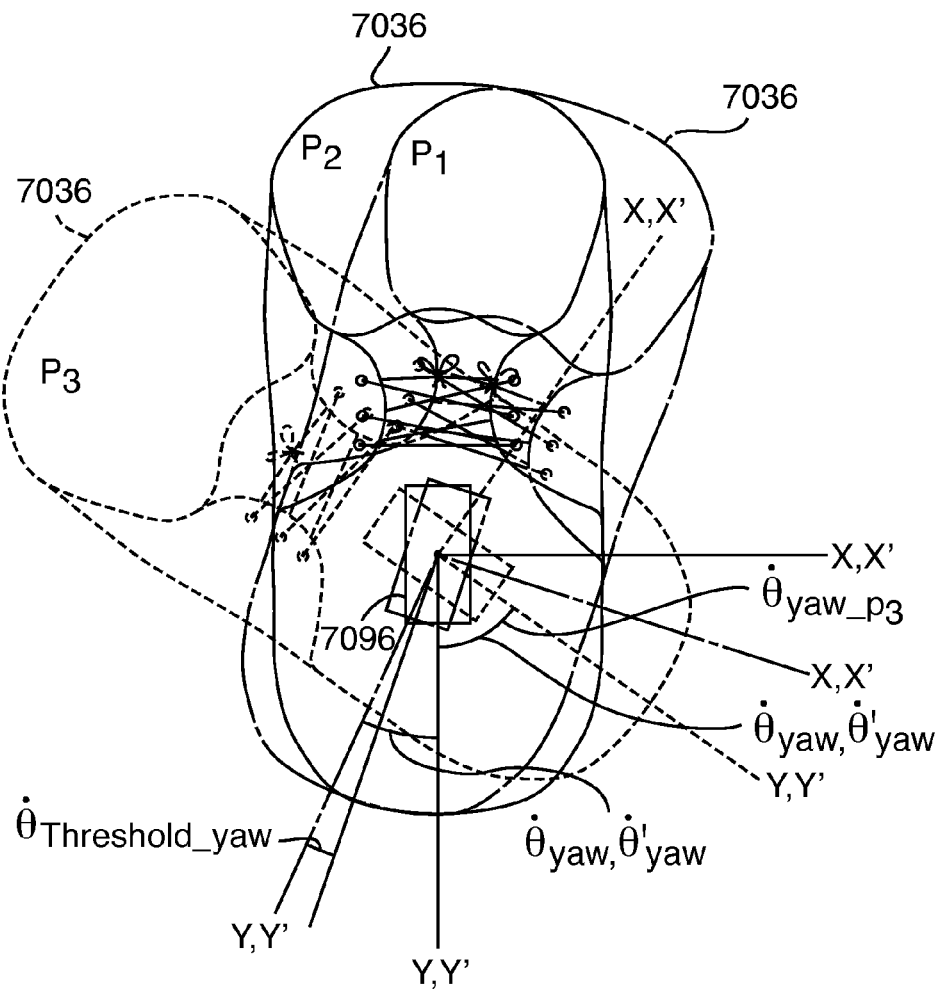
FIG. 11 is a top view of an inertial measurement unit of FIG. 2.

Referring to FIG. 11, each gyroscope 8116, shown in FIG. 4, is able to detect yaw $\dot{\theta}_{Yaw}$ as the rate of angular rotation relative to the Z axis. Thus, yaw $\dot{\theta}_{Yaw}$ about the Z axis is detectable by the IMU 7096 when the user's foot 7021 moves about the Z axis. Unlike the pitch $\theta_{Pitch}$ and roll $\theta_{Roll}$, which are each detected relative to a fixed reference, i.e. the gravitational direction G, the yaw $\dot{\theta}_{Yaw}$ is detected by the gyroscope 7116 with respect to the reference frame of the gyroscope 7116. Thus, the gyroscope 7116 effectively resets its frame of reference after each angular deflection of the IMU 7096. For example, if after moving from the first position $P_1$ to the second position $P_2$, the user then moves the IMU 7096 to a third position $P_3$, the yaw $\dot{\theta}_{Yaw}$ detected by the IMU 7096 as the IMU 7096 moves from the second position $P_2$ to the third position $P_3$ would be relative to the second position $P_2$. This yaw $\dot{\theta}_{Yaw}$ detected by the IMU 7096 may be configured to command the associated device 7012, shown in FIGS. 1A and 1B.

For example, the device module 7017, shown in FIGS. 1A and 1B, may command the associated device 7012 when:

$$|\dot{\theta}_{Yaw}| \geq \dot{\theta}_{Threshold\_Yaw}$$

where, $\dot{\theta}_{Yaw}$ is the yaw detected by the IMU 7096; and $\dot{\theta}_{Threshold\_Yaw}$ is a present minimum yaw angular rotation that must be exceeded to ensure that the detected yaw $\dot{\theta}_{Yaw}$ is a desired command and not due to unintentional movement of the user's foot 7021, shown in FIG. 2, or drifting of the gyroscope 8116, shown in FIG. 4.

Advantageously, since the yaw $\dot{\theta}_{Yaw}$ detected by the gyroscope 8116, shown in FIG. 4, about the Z axis is relative to the previous position of the IMU 7096, rather than a fixed reference frame like the gravitational direction G, shown in FIG. 2, a yaw offset is not necessary, as was the case with detection of the pitch and roll.

In one embodiment, the command generated by the device module 7017, shown in FIGS. 1A and 1B, from the yaw $\dot{\theta}_{Yaw}$ may be a switch that alternates between an "on state" and an "off state" each time $|\dot{\theta}_{Yaw}| \geq \dot{\theta}_{Threshold\_Yaw}$. In another embodiment, yaw $\dot{\theta}_{Yaw}$ may command the device module 7017, shown in FIGS. 1A and 1B, to toggle through a list. For example, each instance that $\dot{\theta}_{Threshold\_Yaw}$ is exceeded, the device module 7017, shown in FIGS. 1A and 1B, may toggle forward through the list if $\dot{\theta}_{Yaw}$ is a positive value and may toggle backward, i.e. in reverse, through the list if $\dot{\theta}_{Yaw}$ is a negative value.

In one embodiment, the command generated by the device module 7017, shown in FIGS. 1A and 1B, may correspond to a movement, $M_{Yaw}$, of the associated device 7012, shown in FIGS. 1A and 1B, if $|\dot{\theta}_{Yaw}| \geq \dot{\theta}_{Threshold\_Yaw}$. For example, when $|\dot{\theta}_{Yaw}| \geq \dot{\theta}_{Threshold\_Yaw}$ the device module 7017, shown in FIGS. 1A and 1B, may command movement $M_{Yaw}$ at a preset velocity in a preset direction, e.g. the device module 7017 may command movement to the right at the preset velocity if $\dot{\theta}_{Yaw}$ is a positive value and may command movement to the left if $\dot{\theta}_{Yaw}$ is a negative value. In this exemplary embodiment for commanding right and left movement, it may also be desirable to halt right and left movement using the detected yaw $\dot{\theta}_{Yaw}$. For example, if the device module 7017 has commanded movement $M_{Yaw}$ to the right, based on a positive $\dot{\theta}_{Yaw}$, a subsequently detected negative $\dot{\theta}_{Yaw}$ that satisfies the relationship $|\dot{\theta}_{Yaw}| \geq \dot{\theta}_{Threshold\_Yaw}$ may generate a command to stop moving to the right, rather than a command to move to the left. From the stopped position, another negative $\dot{\theta}_{Yaw}$ that satisfies the relationship $|\dot{\theta}_{Yaw}| \geq \dot{\theta}_{Threshold\_Yaw}$ would then command leftward movement or, alternatively, a positive $\dot{\theta}_{Yaw}$ that satisfies the relationship $|\dot{\theta}_{Yaw}| \geq \dot{\theta}_{Threshold\_Yaw}$ would then command rightward movement. Similarly, if the device module 7017 has commanded movement $M_{Yaw}$ to the left, based on a negative $\dot{\theta}_{Yaw}$, a subsequently detected positive $\dot{\theta}_{Yaw}$ that satisfies the relationship $|\dot{\theta}_{Yaw}| \geq \dot{\theta}_{Threshold\_Yaw}$ may generate a command to stop moving to the left, rather than a command to move to the right. From the stopped position, a negative $\dot{\theta}_{Yaw}$ that satisfies the relationship $|\dot{\theta}_{Yaw}| \geq \dot{\theta}_{Threshold\_Yaw}$ would then command leftward movement or, alternatively, a positive $\dot{\theta}_{Yaw}$ that satisfies the relationship $|\dot{\theta}_{Yaw}| \geq \dot{\theta}_{Threshold\_Yaw}$ would then command rightward movement.

For exemplary purposes, the pitch $\theta_{Pitch}$, roll $\theta_{Roll}$ and yaw $\dot{\theta}_{Yaw}$ have been described as commanding specific movements in connection with FIGS. 7-11. However, it should be understood that the pitch $\theta_{Pitch}$, roll $\theta_{Roll}$ and yaw $\dot{\theta}_{Yaw}$ may be programmed within the device module 7017, shown in FIGS. 1A and 1B, to command a variety of different movements, and in some embodiments, in response to the user's preferences and customization.

It should be understood that although the use of at least one IMU 7096 for control of the associated device 7012, shown in FIGS. 1A and 1B, is described herein, the at least one IMU 7096 may be used in conjunction with any one or more various devices and/or sensors 7018 to control the associated device 7012. Thus, in some embodiments, the IMU 7096 may be used in conjunction with the sensors 7018, switches, buttons or the like.

In some embodiments, as discussed in connection with sensor module 9015 of FIG. 6, it may be beneficial to include three accelerometers 9114 or a three-axis accelerometer, in the IMU 7096 along with at least one gyroscope 9116 for detecting orientation changes about at least three axes and for enabling walk detection. In an embodiment with IMU 7096 having three accelerometers 9114, the IMU 7096 generates output relating to pitch $\theta_{Pitch}$, roll $\theta_{Roll}$ and yaw $\dot{\theta}_{Yaw}$ in substantially the same manner discussed above in connection with the IMU 8096, shown in FIG. 4, having two accelerometers 8114. However, with the third accelerometer 9114, the IMU 7096 may provide the control apparatus 7010, shown in FIGS. 1A and 1B, with walk detection capability.

Figure 12:
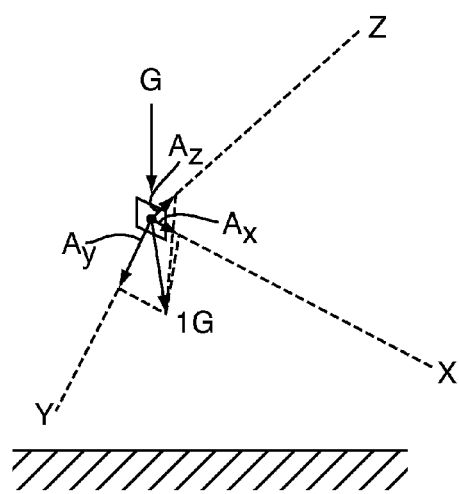
FIG. 12 is a side perspective view of an inertial measurement unit according to an embodiment of the present invention.

Referring back to FIGS. 1A and 1B, when using the IMU 7096 for control of the associated device 7012, walking may be problematic, since walking movement of the user's foot 7021, shown in FIG. 2, will cause the IMU 7096 to sense orientation changes, which the device module 7017 will use to control the associated device 7012. However, walking may be detected by providing an IMU 7096 having a third accelerometer 9114, shown in FIG. 6. Referring to FIG. 2, each of the accelerometers 9114, shown in FIG. 6, may be arranged to measure the acceleration in one of the X, Y or Z directions. Thus, when the user is substantially stationary, the vector sum of the accelerations detected by each of the three accelerometers 9114, shown in FIG. 6, should be substantially equal to 1G. When the Z axis is coincident with the direction of gravity G, the accelerometer 9114 detecting acceleration in the Z direction will detect the entire 1G acceleration due to gravity, since the accelerations in the X and Y directions will be substantially equal to zero. Now, referring to FIG. 12, when the user is stationary, but the direction of gravity G is not coincident with the Z axis, i.e. the user has moved their foot 7021 to command a pitch $\theta_{Pitch}$ and/or roll $\theta_{Roll}$, the vector sum of the accelerations Ax, Ay and Az in the X, Y and Z directions, respectively, will still equal 1G.

If the user begins to walk, the vector sum of the accelerations Ax Ay and Az detected by each of the three accelerometers 9114 will be substantially greater than 1G, since the act of walking will cause additional acceleration, other than gravity, to be detected by the IMU 7096. Thus, once the IMU 7096 detects the accelerations Ax, Ay and Az, the vector sum of the accelerations may be compared to a walk detect limit. In some embodiments, the walk detect limit may be set at approximately 1.2G. If the vector sum of the accelerations is lower than the walk detect limit, the device module 7017, shown in FIGS. 1A and 1B, may command the associated device 7012, shown in FIGS. 1A and 1B, in accordance with the pitch $\theta_{Pitch}$, roll $\theta_{Roll}$ and/or yaw $\dot{\theta}_{Yaw}$ detected by the IMU 7096. However, if the walk detect limit is exceeded by the vector sum of the accelerations, the device module 7017, shown in FIGS. 1A and 1B, will assume the user is walking and may alter the control scheme for the associated device 7012.

Referring back to FIG. 2, in some embodiments, the user may calibrate the sensor module once the user places the sensor module 7015 on the desired body part, such as their foot or feet 7021. This calibration may negate any misalignments of the IMU 7096 on the user's body part, such as foot 7021, for example, by setting the pitch and yaw offset angles discussed above. In some embodiments, the user may place the sensor module 7015 on their foot or feet 7021 and then power the sensor module 7015 "on" to automatically enter a calibration mode. Once in the calibration mode, the user may perform one or more calibration movements with their foot or feet 7021, i.e., "tow up", "heel up", "tilt side to side", etc., to establish a baseline for the range of motion of the user's foot or feet 7021, which may be used, for example, to set motion control gains such as gains $k_1$, $k_2$, $k_3$ and $k_4$ discussed above. These calibration movements and their order of performance are for exemplary purposes only. In other embodiments, different calibration movements and/or a different order of performance of calibration movements may be used, as should be understood by those skilled in the art. In various embodiments, the user may be required to complete a "range of motion" to establish a baseline and for the system to establish the X, Y and Z axes.

In some embodiments of the present invention, the device module 7017 will send a zero command to the sensor module 7015, which the sensor module 7015 may use to redefine its zero position or orientation to be the current position or orientation. For example, the device module 7017, shown in FIGS. 1A and 1B, may send a zero command to the IMU 7096 of the sensor module 7015 by setting a pitch offset, $\theta_{Offset\_Pitch}$, and a roll offset, $\theta_{Offset\_Roll}$. This zero command may be used to compensate for orientation changes of the foot/feet 7021, shown in FIG. 2, for example, if the user is standing on an incline or the like. Thus, the zeroing process may be beneficial for many reasons, including, but not limited to, where the user moves from flat ground to a sloped ground, the controls may interpret this as a command. Therefore, active zeroing eliminates this issue which may otherwise give ruse to unintended commands.

The sensor module of the present invention is advantageous because it is able to detect the orientation of a user's body part, for commanding an associated device, using an IMU having fewer orientation sensors, i.e. accelerometers and/or gyroscopes, than conventional IMUs. This is beneficial because it reduces the overall size of the IMU, which, in turn, reduces the size and weight of the sensor module. Additionally, by reducing the number of orientation sensors as compared to conventional IMUs, the present invention also advantageously reduces both the power required for the IMU and the processor size required to process the signals from the IMU. This also advantageously reduces the size of the sensor CPU and the sensor module battery, thereby further reducing the size of the sensor module. This size reduction beneficially provides for a single-component compact sensor module adapted to be attached on essentially and user body part with minimal discomfort.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A sensor module comprising:
   an IMU having at least one sensor;
   a sensor CPU in communication with the at least one sensor; and
   wherein the sensor CPU receives input signals from the at least one sensor of the IMU; and
   wherein the sensor CPU outputs a pitch, a roll and a yaw of the IMU.

2. The sensor module according to claim 1, wherein the IMU comprises at least three sensors including at least two accelerometers.

3. The sensor module according to claim 2, wherein the third sensor comprises a gyroscope.

4. The sensor module according to claim 1, wherein the at least one sensor comprises an accelerometer.

5. The sensor module according to claim 1, further comprising a power supply for supplying power to the sensor module.

6. The sensor module according to claim 5, wherein the power supply comprises a battery and a power antenna connected to the battery for wirelessly charging the battery.

7. The sensor module according to claim 5, further comprising a support structure comprising the IMU, sensor CPU, and power supply disposed on the support structure.

8. The sensor module according to claim 7, wherein the support structure comprises at least one circuit board.

9. The sensor module according to claim 5, further comprising a housing,
   wherein the IMU, sensor CPU, and power supply are each disposed in the housing.

10. The sensor module according to claim 9, further comprising a strap attached to the housing and adapted to connect the housing to a body part of a user.

11. The sensor module according to claim 9, wherein the housing includes a main portion with the sensor CPU and power supply disposed therein and an IMU portion connected to the main portion by a conduit, the IMU portion having the IMU disposed therein.

12. A sensor module adapted to be attached to footwear, the sensor module comprising:
   a support comprising at least one circuit board;
   at least one sensor disposed on the support and adapted to detect orientation;
   a sensor CPU disposed on the support and in communication with the at least one sensor through the at least one circuit board; and
   a power supply having a battery disposed on the support for supplying power to the sensor module through the circuit board.

13. The sensor module according to claim 12, wherein the sensor CPU receives input signals from the at least one sensor; and
   wherein the sensor CPU outputs a pitch, a roll and a yaw of the sensor module through a sensor module communicator.

14. The sensor module according to claim 12, further comprising at least a second sensor;
   wherein the at least two sensors are accelerometers detecting accelerations in two axes.

15. The sensor module according to claim 14, further comprising at least a third sensor;
   wherein the third sensor is a gyroscope.

16. The sensor module according to claim 12, comprising at least three sensors that are accelerometers.

17. The sensor module according to claim 12, wherein the power supply includes a power antenna connected to the battery for wirelessly charging the battery.

18. A control system for controlling an associated device, the control system comprising:
   a sensor module comprising:
      an IMU having at least one sensor adapted to detect orientation in at least one axes; and
      a sensor CPU in communication with the IMU; and
   a device module in communication with the sensor module, the device module in communication with the associated device;
   wherein the device module receives a pitch signal, a roll signal and a yaw signal from the sensor module and commands the associated device based on at least one of the pitch signal, the roll signal and the yaw signal.

19. The control system according to claim 18, wherein the sensor module is in wireless communication with the device module.

20. The control system according to claim 18, wherein the IMU includes three sensors including at least two accelerometers detecting accelerations in at least two orthogonal axes.

* * * * *